United States Patent [19]
Korbanka et al.

[11] 4,202,830
[45] May 13, 1980

[54] ORGANOTIN HALIDES

[75] Inventors: Helmut Korbanka, Adelsried; Franz Scheidl, Gersthofen, both of Fed. Rep. of Germany

[73] Assignee: Hoechst Aktiengesellschaft, Frankfurt am Main, Fed. Rep. of Germany

[21] Appl. No.: 931,678

[22] Filed: Aug. 7, 1978

[30] Foreign Application Priority Data

Aug. 9, 1977 [DE] Fed. Rep. of Germany ....... 2735757

[51] Int. Cl.$^2$ ................................ C07F 7/22
[52] U.S. Cl. ................................ 260/429.7
[58] Field of Search ...................... 260/429.7

[56] References Cited

U.S. PATENT DOCUMENTS

| | | | |
|---|---|---|---|
| 3,440,255 | 4/1969 | Matsuda et al. | 260/429.7 |
| 4,080,362 | 3/1978 | Hutton et al. | 260/429.7 |
| 4,080,363 | 3/1978 | Hutton et al. | 260/429.7 X |
| 4,105,684 | 8/1978 | Hutton et al. | 260/429.7 |

Primary Examiner—Helen M. S. Sneed
Attorney, Agent, or Firm—Connolly and Hutz

[57] ABSTRACT

The invention provides novel organotin halides obtained by reaction of tin and hydrogen chloride with those olefins which carry a carbonyl group in adjacent position to the olefinic double bond and which are substituted in addition by at least one carboxylate group not adjacent to the double bond.

3 Claims, No Drawings

ORGANOTIN HALIDES

The present invention relates to novel organotin halides and a process for the preparation thereof.

The industrial processes hitherto known for manufacture of organotin halides such as dibutyl-tin dichloride, monobutyl-tin trichloride or dioctyl-tin dichloride, involve safety risks and thus require great expenditure, because they are based on the Grignard, aluminum-alkyl, or Wurtz syntheses. According to these syntheses, tetra-alkyl or tetra-aryl compounds are prepared from alkyl or aryl chlorides and tin tetrachloride (Grignard, Wurtz), or from aluminum-alkyls and tin tetrachloride, and the compounds so obtained are then converted to the intended tri-, di- and mono-organotin chlorides according to comproportioning processes.

Less problematic are other processes based on metallic tin. According to this direct synthesis, tin is converted to alkyl-tin halides by means of alkyl halides. However, this preparation method has various disadvantages, for example the required elevated reacion temperatures, especially when alkyl chlorides are used, or the necessity of employing catalysts such as N- and P-containing compounds together with iodine compounds (German Auslegeschriften Nor. 1,240,081 and 1,274,580), organic phosphites (German Offenlegungsschrift No. 1,468,494), ammonium or phosphonium compounds (German Auslegeschrift No. 1,277,255 and German Offenlegungsschrift No. 1,816,549), mixtures of metallic magnesium and iodine or alkyl iodides (U.S. Pat. No. 3,440,255), etc..

Furthermore, organotin halides can be prepared by reaction of metallic tin and hydrogen halide with activated olfins. These olefins are of the formula

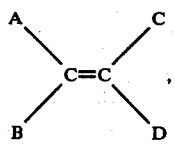

in which B, C and D each are hydrogen or a hydrocarbon radioal, and the radical A, optionally also the radical B; contains a carbonyl group adjacent to the olefinic double bond (German Offenlegungsschrift No. 2,607,178). The mixtures of organotin di- and trihalides obtainable with high yield according to this process, however, are contaminated in some cases, especially when the reaction is carried out at elevated temperature, by polymers of the starting olefins formed in side reactions, and these by-products practically cannot be eliminated. When, after processing of the organotin halides to organotin stabilizers, these by-products finally are introduced into plastics compositions, they cause generally undesirable turbidity of the plastic material.

It has now been found that hitherto unknown organotin halides surprisingly free from polymers of the corresponding olefins are obtained in the form of mixtures of di- and trihalides when using olefins of a different kind which, although containing a carbonyl group in vicinal position to the olefinic double bond, are additionally substituted by at least one carboxylate group not adjacent to the double bond.

The novel organotin compounds have the formulae

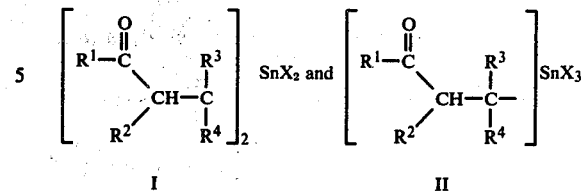

in which
$R^1$ is OH, halogen, $NH_2$, an alkyl- or arylamino radical, an O-alkyl or O-aryl radical, both the latter radicals being unsubstituted or substituted by aryl or alkyl and optionally carrying as additional substituents halogen or a hydroxy, thioether, ether and/or carboxyl group;

$R^2$ to $R^4$, being identical or different, each represent 0 to 2 hydrogen atoms, or alkyl radicals having from 1 to 20 carbon atoms; at least one of these radicals, however, being a $$-(CH_2)_n-\overset{O}{\underset{\|}{C}}-R^1$$

group where n is an integer of from 1 to 15;
X is chlorine, bromine or iodine,
and the radicals $R^1$ to $R^4$ and X corresponding to one another in the components I and II of the mixture are always identical.

Examples of $R^1$ are —OH, —$NH_2$, —Cl, —Br, —I, alkyl and arylamino radicals such as —$NH(CH_3)$,

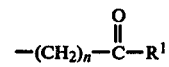

—$N(C_2H_5)_2$,

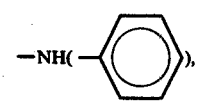

O-alkyl radicals such as —$OCH_3$, —$OC_2H_5$, —$OC_8H_{17}$,

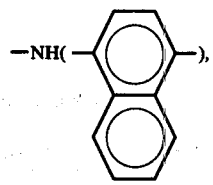

—O—$CH_2$—$CH_2$—OH,

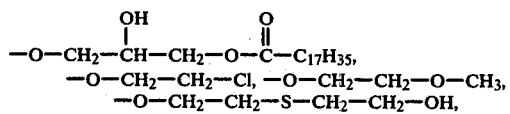

—O—$CH_2$—$CH_2$—Cl, —O—$CH_2$—$CH_2$—O—$CH_3$,
—O—$CH_2$—$CH_2$—S—$CH_2$—$CH_2$—OH,

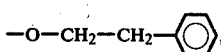

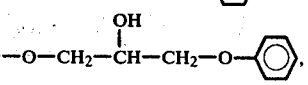

or O-aryl radicals such as 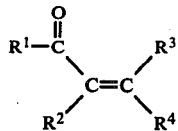.

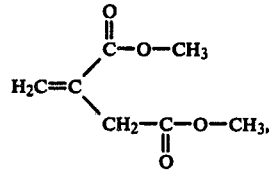

in which $R^1$ to $R^4$ are as defined above.

Some typical representatives of suitable olefins are the following:

| 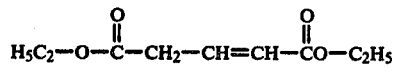 Itaconic acid-dimethyl ester | 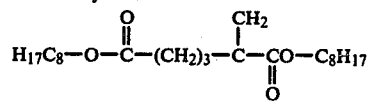 2-Methylene glutaric acid-dibutyl ester |
|---|---|
| $H_5C_2-O-\overset{O}{\underset{\|}{C}}-CH_2-CH=CH-\overset{O}{\underset{\|}{C}}O-C_2H_5$ Glutaconic acid diethyl ester | 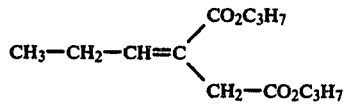 2-Methylene adipic acid di-n-octyl ester |
| $CH_3-CH_2-CH=C\begin{smallmatrix}CO_2C_3H_7\\ \\CH_2-CO_2C_3H_7\end{smallmatrix}$ Propylidene-succinic acid-dipropyl ester | $HO_2C-(CH_2)_8-CH=CH-CO_2H$ Traumatic acid |
| $HO_2C-(CH_2)_{12}-CH=CH-CO_2H$ Tetradecene-1-dicarboxylic acid-(1,14) | 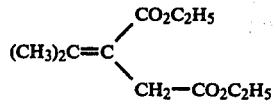 Teraconic acid-diethyl ester |

Preferred olefins are the esters of itaconic acid.

Examples of $R^2$ to $R^4$ are at least one radical of the structure

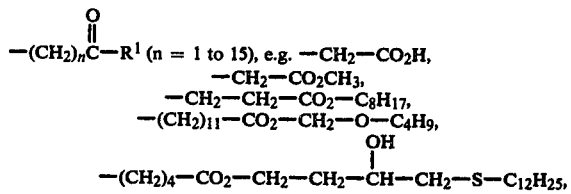

furthermore hydrogen, methyl, ethyl, propyl, hexyl, dodecyl or octadecyl.

Preferred are those compounds in which $R^1$ is an O-alkyl radical having from 1 to 40, preferably 1 to 30, and especially 1 to 20 carbon atom, and $R^3$ and $R^4$ each are hydrogen, $R^2$ is the radical

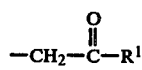

($R^1$ being in the above preferential range), and X is chlorine.

The novel organotin halides are prepared by reacting metallic tin and hydrogen halide with an olefin of the formula The reaction may be carried out without solvents, or in, for example, ethers such as diethyl ether, tetrahydrofuran, dioxan or 1,2-dimethoxy-ethane; in esters such as ethyl acetate; in ketones such as acetone or ethylmethylketone; in alcohols such as methanol, ethanol or butanol; in aromatic hydrocarbons such as toluene, xylene, chlorobenzene etc.; in aliphatic hydrocarbons such as gasolines, chlorine-containing aliphatic substances such as chloroform or carbon tetrachloride; in water (in the form of concentrated hydrochloric acid) or in an excess of the olefin.

The hydrogen halide may be introduced into the reactor in the form of a gas or an aqueous solution, especially a concentrated aqueous solution. Hydrogen chloride is preferably used.

Metallic tin may be employed for the reaction in any form; however, pulverulent tin is preferred because of its large, that is, reactive, surface. On the other hand, tin granules are likewise suitable.

The reaction is carried out by either introducing first the olefin, the solvent and the tin into the reactor, and adding the hydrogen halide, or by saturating the olefin/solvent mixture with hydrogen halide and adding the tin only then.

The reaction is carried out at temperatures of from 0° to 150° C., preferably of from about 0° to 100° C., especially 20° to 80° C.

The organotin halides obtained in the reaction are mixtures of di- and mono-organotin halides of the formulae (R)$_2$SnHal$_2$ and (R)SnHal$_3$, the radical R having probably the following structure:

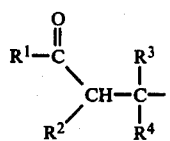

which can be assumed to be correct on account of the analytic and spectroscopic data, the course of the reaction and the chemical composition of these olefins. The approximate ratio of di- and mono-organotin compound can be calculated on the chlorine content of the reaction products; it varies within wide limits and depends on the reaction conditions (for example on the solvent used and the feeding rate of the hydrogen halide). Generally, the amount of mono-organotin trichloride (R)SnCl$_3$ in the reaction mixture is from 0.01 to 80% by weight, that is, the ratio of di-organotin chloride to mono-organotin chloride is about 1:0 to 1:4.

The di- and trihalides may be separated according to known methods, for example by fractional crystallization. However, separation can be omitted, especially in the case where the reaction products are processed to tin stabilizers.

The novel organotin halides are interesting intermediate products which are suitable for example for the synthesis of plant protecting agents and pesticides, or as starting products for the manufacture of heat stabilizers for plastics processing.

The following Examples illustrate the invention.

EXAMPLE 1

79 g (0.5 mol) itaconic acid dimethyl ester, 29.6 g (0.25 mol) tin powder and 150 ml diethyl ether are introduced into a three-necked flask having a capacity of 500 ml and provided with agitator, inside thermometer and gas inlet tube. Within 2.5 hours, a total of 36.5 g (1 mol) anhydrous, gaseous hydrogen chloride was uniformly introduced with thorough agitation and cooling, at a temperature of 20° to 25° C. Agitation was continued for a further 10 hours at the same temperature. At the end of this period, no tin could be detected any more. Subsequently, the ether and the excess hydrogen chloride were removed under water jet vacuum. A light-colored highly viscous liquid remained which did not contain tin-II chloride.

| Yield: | 135.5 g organotin chloride mixture |
|---|---|
| Analyses: | 19.7% total chlorine |
| | 19.5% saponifiable chlorine |
| | 21.8% tin |
| Iodine number: | 1 g iodine/100 g substance. |

Calculation of the amount of (R)$_2$SnCl$_2$ and (R)SnCl$_3$ on the chlorine content found:

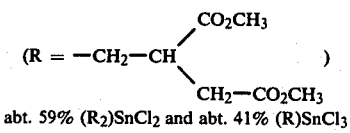

abt. 59% (R$_2$)SnCl$_2$ and abt. 41% (R)SnCl$_3$

It results furthermore from the chlorine analyses that practically no hydrogen chloride has added on the double bond of the itaconic acid dimethyl ester. The iodine number found proves that practically no itaconic acid ester is present any more.

When the product is heated in a sufficient amount of toluene, a clear solution is formed, from which, on cooling, the compound having the formula

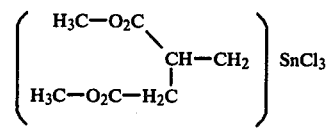

precipitates in the form of white crystals having a melting point of 144°–146° C.

EXAMPLE 2

197.5 g (1.25 mols) itaconic acid dimethyl ester and 29.6 g (0.25 mol) tin powder were introduced into the apparatus as described in Example 1, and heated to 45° C. Within 4 hours, at this temperature, 36.5 g (1 mol) hydrogen chloride gas were uniformly introduced. After a further 4 hours agitation at 45° C., no tin was present any more. Subsequently, the excess hydrogen chloride was removed, and the itaconic acid dimethyl ester residue was distilled off at a bath temperature of 120° C. and under a pressure of 10 mm Hg. A light-colored, viscous product free from tin-II chloride remained, which did not contain any polymers either.

| Yield: | 127.4 g organotin chloride mixture |
|---|---|
| Analyses: | 17.8% total chlorine |
| | 17.7% saponifiable chlorine |
| | 23.0% tin |
| Iodine number: | 1 g iodine/100 g substance |
| calculated on the chlorine value: | abt. 72% (R)$_2$SnCl$_2$ |
| | abt. 28% (R)SnCl$_3$ |

EXAMPLE 3

Operations were as indicated in Example 2; however, the temperature was from 120° to 125° C.

The reaction product corresponded to that of Example with respect to all analysis data, and it dit not contain any trace of polymethyl itaconate either.

EXAMPLE 4

60.5 g (0.25 mol) itaconic acid di-n-butyl ester, 14.8 g (0.125 mol) tin powder and 300 ml toluene were introduced into the apparatus described in Example 1, and heated to 80° C. At this temperature, and within 6 hours, 24 l of hydrogen chloride gas were introduced. Subsequently, agitation was continued for 20 hours at 80° C., after which period of time the solution contained only traces of metallic tin. After work-up, a light-colored, viscous liquid was obtained as reaction product.

| Yield: | 87.4 g organotin chloride mixture |
|---|---|
| Analyses: | 13.7% total chlorine |
| | 13.7% saponifiable chlorine |
| | 16.8% tin |
| Iodine number: | 1.2 g iodine/100 g substance |
| Calculated on the chlorine value: | abt. 87% (R)$_2$SnCl$_2$ |
| | abt. 13% (R)SnCl$_3$ |

$$R = -CH_2-CH\begin{array}{c}CH_2CO_2C_4H_9\\|\\CO_2C_4H_9\end{array}$$

EXAMPLE 5

121 g (0.5 mol) itaconic acid di-n-butyl ester, 29.6 g (0.25 mol) tin powder and 150 ml 1,4-dioxan were introduced into the apparatus described in Example 1, and heated to 80° C. At this temperature, gaseous hydrogen chloride (5 l/hour) was introduced for 5 hours. After this period of time, no tin was present any more. After work-up, a light-colored, viscous liquid remained as reaction product.

| Yield: | 179.6 g organotin chloride mixture |
|---|---|
| Analyses: | 15.4% total chlorine |
| | 15.2% saponifiable chlorine |
| | 16.4% tin |
| Iodine number: | 1.3 g iodine/100 g substance |
| Calculated on the chlorine value: | abt. 70% $(R)_2SnCl_2$ |
| | abt. 30% $(R)SnCl_3$ |

EXAMPLE 6

According to the operation mode of Example 1, 128.0 g (0.5 mol) 2-methyleneglutaric acid di-n-butyl ester were reacted with 29.6 g (0.25 mol) tin and 36.5 g (1 mol) hydrogen chloride.

| Yield: | 179.6 g organotin chloride mixture in the form of a yellowish liquid |
|---|---|
| Analyses: | 12.5% total chlorine |
| | 12.4% saponifiable chlorine |
| | 16.3% tin |
| Iodine number: | less than 1 g iodine/100 g substance |
| calculated on the chlorine value: | abt. 93% $(R)_2SnCl_2$ |
| | abt. 7% $(R)SnCl_3$ |

$$R = -CH_2-CH\begin{matrix}CH_2-CH_2-CO_2-C_4H_9\\ \\ CO_2C_4H_9\end{matrix}$$

EXAMPLE 7

60.5 g (0.25 mol) itaconic acid di-n-butyl ester and 14.8 g (0.125 mol) tin powder were introduced into a three-necked flask having a capacity of 250 ml and provided with agitator, inside thermometer and dropping funnel. At a temperature of about 20° C. and within 1 hour, 29.6 g 37% aqueous hydrochloric acid, corresponding to 10.95 g (0.3 mol) hydrogen chloride, were added dropwise. Agitation was continued for 10 hours at room temperature. The reaction mixture nearly free from tin powder residues was extracted with 150 ml toluene, and the toluene phase was separated. The toluene was removed at 100° C./10 mm Hg. A brownish liquid was obtained as residue.

| Yield: | 80.0 g organotin chloride mixture |
|---|---|
| Analyses: | 12.4% total chlorine = saponifiable chlorine |
| | 19.3% tin |
| Iodine number: | 1.2 g iodine/100 g substance |
| Calculated on the chlorine value: | abt. 100% $(R)_2SnCl_2$ |

$$R = -CH_2-CH\begin{matrix}-CH_2-CO_2C_4H_9\\ \\ CO_2C_4H_9\end{matrix}$$

EXAMPLES 8 to 14

Operations for the Examples listed in the following Table were as indicated in Example 1. In each case, 29.6 g (0.25 mol) tin and 36.5 g (1 mol) hydrogen chloride gas were used.

| | | Reaction conditions | | | | Reaction products | | | | calculated on chlorine value |
|---|---|---|---|---|---|---|---|---|---|---|
| Ex. No. | Olefin | g | mol | Solvent | React. temp. °C. | g | % Cl | % Sn | IN | form | % $(R)_2SnCl_2$/ % $(R)SnCl_3$ |
| 8 | itaconic acid | 65.0 | 0.5 | (1) | 20 | 111.6 | 24.2 | 26.2 | <1 | solid | 50/50 |
| 9 | itaconic acid dichloride | 83.5 | 0.5 | (2) | 10 | 131.0 | 41.0 | 22.6 | <1 | liquid | 100/0 |
| 10 | itaconic acid-di-n-octyl ester | 177.0 | 0.5 | (3) | 80 | 230.6 | 10.4 | 12.7 | 0 | liquid | 75/25 |
| 11 | itaconic acid-di-anilide | 152.0 | 0.5 | (4) | 40 | 208.0 | 12.5 | 14.1 | — | solid | 68/32 |
| 12 | Glutaconic acid-di-n-octyl ester | 177.0 | 0.5 | (5) | 60 | 229.8 | 10.1 | 12.7 | 0 | liquid | 79/21 |
| 13 | dimethyl-itaconic acid-di-n-butyl ester | 135.0 | 0.5 | (2) | 20 | 185.6 | 11.2 | 15.7 | 1 | liquid | 87/13 |
| 14 | n-hexyl-itaconic acid-di-ethyl ester | 135.0 | 0.5 | (2) | 40 | 188.8 | 12.7 | 15.6 | 1 | liquid | 75/25 |

Solvents:
(1) acetone
(2) diethyl ether
(3) toluene
(4) 1,2-dimethoxyethane
(5) 1,4-dioxan This Example is intended to show the utility of the novel organo tin halides as starting products for the manufacture of heat stabilizers for plastics processing and the advantageous attributes of these stabilizers.

EXAMPLE 15

40.8 g (0.2 mol) thioglycolic acid-2-ethylhexyl ester, 36.0 g (0.2 chlorine equivalent) of the organo tin chloride mixture obtained according to Example 1 and 300 ml toluene were introduced into a three-necked flask having a capacity of 500 ml provided with agitator, inside thermometer and dropping funnel. At 20° C., a solution of 20.2 g (0.2 mol) triethylamine in 50 ml toluene was added dropwise. Subsequently, agitation was continued for 2 hours at room temperature. The precipitate formed (27.5 g triethylammonium chloride) was then suctionfiltered. After having distilled off the toluene, the organo tin stabilizer was isolated from the filtrate in the form of a yellowish liquid.

| Yield: | 69.5 g organo-tin-2-ethylhexylthioglycolate |
|---|---|

-continued

Analysis: 11.3% Sn
0.1% Cl lizers, at identical amounts of tin in the formulation and corresponding residues, have a PVC-stabilizing action comparable with that of known dibutyltin stabilizers, but have less influence on the transparency.

| Stabilizer | parts | = g Sn | Dynamic thermostability discoloration of a rough sheet at a laminating time of | | | | | | | |
|---|---|---|---|---|---|---|---|---|---|---|
| | | | 5' | 10' | 15' | 20' | 25' | 30' | 35' | 40' |
| | | | to color number | | | | | | | |
| from substance according to Example 1 | 1.15 | 0.130 | 1[(1)] | 1 | 1 | 1–2 | 2 | 3 | 3–4 | 5 |
| comparative test with di-butyltin-bis-2-ethylhexylthioglycolate | 0.70 | 0.130 | 1[(2)] | 1 | 1–2 | 2–3 | 2–3 | 3 | 3–4 | 5 |
| comparative test with di-butyltin-bis-n-dodecylmercaptide | 0.70 | 0.130 | 1[(2)] | 2 | 2 | 2–3 | 3–4 | 3–4 | 5 | — |

[(1)]rough sheet completely transparent
[(2)]rough sheet slightly opaque

| Stabilizer | parts | = g Sn | Static thermostability discoloration of a rough sheet in drying cabinet at a tempering time of | | | | | |
|---|---|---|---|---|---|---|---|---|
| | | | 0' | 20' | 30' | 40' | 50' | 60' |
| | | | to color number | | | | | |
| from substance according to Example 1 | 1.15 | 0.130 | 1 | 2 | 2–3 | 3 | 3–4 | 5 |
| comparative test with di-butyltin-bis-2-ethyl-hexylthioglycolate | 0.70 | 0.130 | 1 | 2 | 2 | 3 | 4 | 5 |

The stabilizing effect of the organo tin compound is shown in the processing of polyvinyl chloride. The parts indicated are by weight.

100 Parts each of a suspension polyvinyl chloride having a K value of 68 were mixed with 0.4 part calcium stearate, 0.4 part hydrocarbon wax having a dropping point of about 90° C., and 1,15 parts of the organo tin stabilizer (=0,130 g Sn). For a comparison, known tin stabilizers were tested under the same conditions.

For determining the dynamic thermostability, the mixtures were applied to a laboratory two-roll mill heated at 180° C., and laminated at 20 rpm to a rough sheet within one minute. In intervals of 5 minutes, samples were taken from the rough sheet and the color was compared with that of an internal color scale. The individual tests were carried out until the rough sheet had become dark brown to black.

In order to determine the static thermostability, a rough sheet was first manufactured from the mixtures according to the above operation mode, and laminated on the mill for a further 10 minutes at 180° C. Subsequently, test specimens having a thickness of about 0.5 mm and a diameter of 30 mm were cut from the sheet taken off the roll. The specimens were wrapped with an aluminium sheet and tempered at 180° C. in a drying cabinet with air circulation. In intervals of 10 minutes, a specimen each was removed and its color compared with the color scale.

The numbers of the color scale used represent:
1 = transparent
2 = slightly yellowish
3 = distinct yellow color
4 = dark yellow to brown
5 = dark brown to black.

The test conditions and the results are listed in the following Tables. As results from the Tables, the stabi-

What is claimed is:
1. Mixture of organotin halides of the formulae

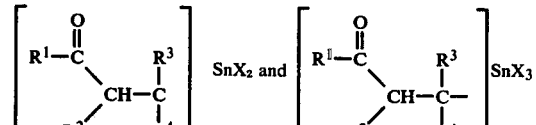

I   II in which
$R^1$ is OH, halogen, $NH_2$, an alkyl- or arylamino radical, an O-alkyl or O-aryl radical, both the latter radicals being unsubstituted or substituted by aryl or alkyl which may also carry as additional substituents halogen or hydroxy,
$R^2$ to $R^4$, being identical or different, each represent hydrogen with their sum being 0 to 2 hydrogen atoms, or alkyl radicals having from 1 to 20 carbon atoms; at least one of these radicals, however, being a

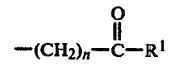

group where n is an integer of from 1 to 15;
X is chlorine, bromine or iodine,
and the radicals $R^1$ to $R^4$ and X corresponding to one another in the components I and II of the mixture are always identical.

2. Mixture of organotin halides as claimed in claim 1, wherein in both components $R^1$ is an O-alkyl group having from 1 to 40 carbon atoms, $R^2$ is

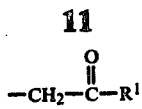
($R^1$ being as defined in this claim), and $R^3$ and $R^4$ each are hydrogen.
3. Mixture of organotin halides as claimed in claim 1 wherein the weight ratio of component I to component II is from 1:0.01 to 1:4.
* * * * *